United States Patent [19]
Hadley

[11] Patent Number: 5,643,236
[45] Date of Patent: Jul. 1, 1997

[54] LEG UNDERPANT FOR SUPPORTING FLUID COLLECTION BAG

[76] Inventor: Jack D. Hadley, Box 337, Dewey, Okla. 74029

[21] Appl. No.: 421,670

[22] Filed: Apr. 12, 1995

[51] Int. Cl.$^6$ .................................................. A61M 1/00
[52] U.S. Cl. .................. 604/353; 604/327; 604/346; 128/DIG. 15; 128/DIG. 24; 4/144.3
[58] Field of Search ...................................... 604/317, 322, 604/327, 331, 332, 339, 340, 343, 345, 346, 347, 353, 385.1; 2/250; 4/144.1, 144.2, 144.3; 224/216, 222; 128/760, DIG. 15, DIG. 24

[56] References Cited

U.S. PATENT DOCUMENTS

| | | |
|---|---|---|
| 3,897,785 | 8/1975 | Barto, Jr. . |
| 4,511,358 | 4/1985 | Johnson, Jr. et al. . |
| 4,753,647 | 6/1988 | Curtis .................... 604/385.1 |
| 5,053,027 | 10/1991 | Mandfredi . |
| 5,087,251 | 2/1992 | Heyman et al. . |
| 5,234,420 | 8/1993 | Horton et al. . |
| 5,439,456 | 8/1995 | Fabricant ................... 604/327 |

OTHER PUBLICATIONS

*Home Health Care Products*, Suburban Ostomy Supply Co., Inc., 1993, pp. 38, 44.
St. Louis Ostomy Distributors, Spring, 1994, pp. 46, 49.

Primary Examiner—P. Zuttarelli
Attorney, Agent, or Firm—Head, Johnson & Kachigian

[57] ABSTRACT

A holder for a urinary drainage bag for securing the bag to a patient's leg. The weight of the urinary drainage bag is supported by a waistband which encircles the patient's waist. The urinary drainage bag is affixed to a partial pantleg which is suspended from the waistband. The partial pantleg is split and adjustably encircles the patient's thigh. The partial pantleg is comprised of a twilled fabric and prevents a typically plastic or vinyl urinary drainage bag from making contact with the patient's thigh. The urinary drainage bag is affixed to the partial pantleg by means of a plurality of buttons provided on the partial pantleg. The buttons are arranged so that as the urinary drainage bag expands the buttonholes formed integrally with the urinary drainage bag will slide with respect to the buttons and not pull or tug on the partial pantleg. The partial pantleg need not be tightly secured to the wearer's thigh in order to be effective. Therefore, the urinary drainage bag holder may be comfortably worn for extended periods of time.

2 Claims, 3 Drawing Sheets

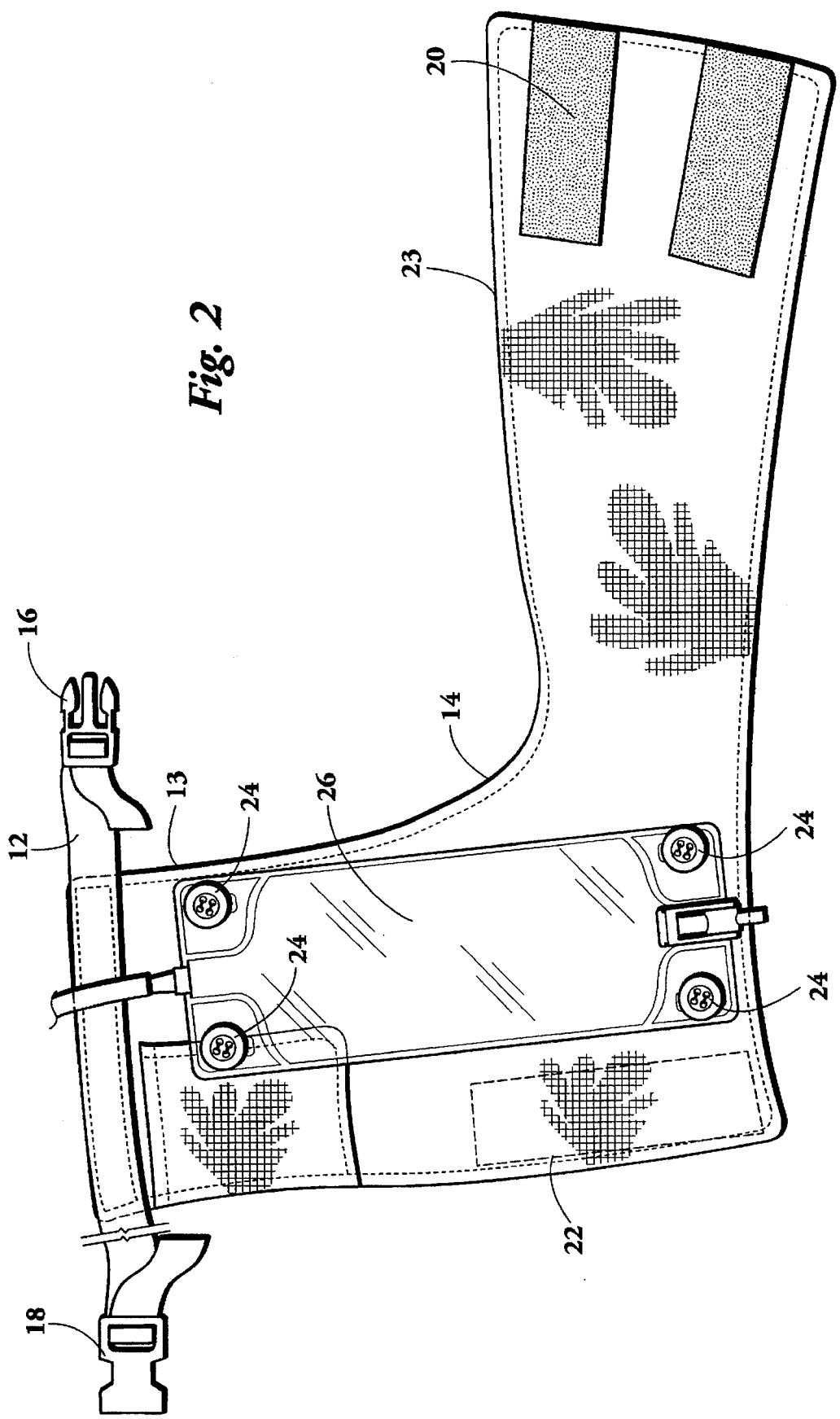

LEG UNDERPANT FOR SUPPORTING FLUID COLLECTION BAG

BACKGROUND OF THE INVENTION

1. Field of the Invention

The invention relates to a urine bag carrier to be worn by an incontinent person for carrying a urine bag on the leg. More specifically, this invention is directed to a fabric undergarment to carry a urine bag. A waistband supports the weight of the urine bag from a person's waist, and the garment loosely envelopes the person's thigh.

2. Prior Art.

Those individuals who are afflicted with certain urological diseases so that the urinary tract is blocked or loses its ability to retain the natural discharge of urine from the body are usually provided with a device for collecting and storing urine. Common methods comprise fitting the patient with an indwelling urinary bladder drainage catheter or an external catheter that are connected by means of a long extension tube to a vinyl or latex urine collecting bag. The collecting bag is often supplied with straps so that the bag can be affixed to the thigh or calf of the patient.

The urine collecting bag is typically rectangular in shape and is provided with an inlet orifice located in the top portion and a drain valve located in the bottom. Typically, the open end of the urinary bladder catheter is connected to the inlet orifice of the bag via an elastomeric tube. The urine enters the bag through the top inlet orifice and is typically drained from the bag through a bottom swing valve which is usually formed of a rigid plastic material. The urinary drainage bag typically holds about 300 ml of urine. The bag is normally held to the thigh of the patient by means of two elastic rubber straps. Although this type of collection device can be hidden from view underneath the patient's clothing, the device has several disadvantages. First, the rubber straps have a tendency to curl up and roll down the patient's leg. This problem is intensified as the bag is filled with urine and becomes heavy. As the bag migrates down a patient's leg, the catheter may be disturbed. Continuous shifting and moving of the bag are accompanied by constant pulling or tugging on the catheter attached thereto. Such constant movement of the catheter can produce irritation along the inner surface of the bladder that, in turn, may cause chronic bleeding. This bleeding may directly contribute to infection of the bladder, prostate, urethra and cystotomy stoma or opening. Even when the patient is in a horizontal position, when the bag becomes half full, it begins to shift and pull the attached catheter. This leads to bladder spasms, pain, loss of sleep, etc. Furthermore, when the bag is filled to capacity overnight, often it shift to rest on the mattress. As a result, the bag is without any effective support. when the patient struggles to rise and empty the bag. Each motion causes movement in the bag which is accompanied by sharp pain as the bag pulls on the catheter which moves within the bladder cavity. Second, the rubber straps, if worn for an extended period of time, cause primary skin irritation due to the pressure, heat, friction and lack of air circulation between the straps and the patient's skin. Third, since the straps are elastic, they are incapable of holding up the weight of the bag as it is filled with urine, even if the straps lay flat against the patient's thigh and are positioned high up on the thigh. Also as a consequence of the elastic nature of the straps, the position of and tension on the straps must be constantly adjusted as the bag fills with urine. On the other hand, if the straps are stretched too tightly around the leg, pain may result as well as restricted blood circulation in the leg.

Fourth, if the bag becomes too full and the straps fail, the bag may fall, resulting in urine spilling out of the urine bag or inflicting severe pain in the patient as the indwelling catheter is subjected to a sharp outward pull.

Furthermore, the positioning of the urine bag flat against the patient's thigh has numerous disadvantages. The large surface area of the bag in constant contact with the skin can cause irritation, chafing, itching and even infection. Small amounts of urine leaked from the catheter/bag inlet connection can seriously complicate the problem.

An additional problem is that as the bag fills, the urine is collects at the bottom portion thereof, causing the bottom portion to bulge, which forces the lower edge of the bag to curl inwardly, i.e. toward the patient. This forces the rigid drain valve to press against the patient's skin. This pressure increases as the bag fills with urine. It has been found that when a typical 300 ml capacity bag is filled to about 75 ml, the weight becomes too great for the rubber straps to hold the bag firmly. This leads to shifting or sliding of the bag and results in the patient's discomfort. Many patients feel compelled to frequently empty the bag as a result. This leads to inefficient use of the bag volume.

From the above description, it is clear that the conventional method of securing a urine bag to the patient's thigh by means of elastic straps is highly painful to the patient and needs much improvement. The present invention is made to correct all of the above defects found in connection with the conventional method.

The disposable plastic bag is customarily clamped or held to the leg of a patient by elastic latex bands tightly encircling the patient's leg. This method, employed in earlier urine collecting apparatus, constricts the leg, and tends to reduce blood circulation in the leg. As a result, this method is uncomfortable to the wearer. The bands are prone to cause irritation of the skin by causing blisters and pulling body hair. Consequently various harness systems for supporting a urine collection bag from the waist have been developed.

One such system is discussed in U.S. Pat. No. 3,897,785 to Barto. Barto shows a harness support system for a disposable urine bag. The system has a separate, disposable, urine collection bag attached to a support sheet. The sheet is designed to hang from art adjustable belt that encircles the wearer's waist when in use. Barto also shows leg bands designed to fit around the patient's leg to secure the support sheet to the leg, with the urine bag affixed thereto. These leg bands tend to be a constant source of irritation and discomfort to the patient.

U.S. Pat. No. 5,087,251 to Hayman shows a disposable urine drainage bag and support harness system. The Hayman invention teaches a urine drainage bag that is formed integrally with a plastic support sheet. The plastic support sheet is not provided with a means to attach the drainage bag to the leg of the patient. However, the entire support sheet is suspended from the waist and is in contact with the leg of the patient. The support sheet is constructed of plastic, which does not "breathe" and is therefore a source of discomfort to the patient especially in hot weather.

U.S. Pat. No. 4,511,358 to Johnson teaches a urine bag carrier that comprises a pouch with a stretchable front panel. The Johnson device provides a waist encircling belt which supports a pouch via straps for holding a urine bag. Additionally, the urine bag is secured to the leg of the patient by horizontal straps which encircle the leg of the wearer. The urine bag holding pouch is provided with a stretchable material to firmly hold the bag within the pouch. The stretchable material comprising the front panel of the pouch exerts a compressive force on the urine bag, especially when the bag becomes full. Additionally, the leg encircling straps are irritating and uncomfortable to the patient.

U.S. Pat. No. 5,234,420 to Horton teaches a collection chamber support device. This device also teaches straps which encircle the thigh of the wearer that are uncomfortable to the patient.

Another method utilized as a urinary leg bag holder are elastic "sleeves" that encircle the leg of the wearer. An example of such a device is UROCARE® product no. 6384. This holder is a 95% cotton, 5% lycra "sleeve" which has broad elasticated cotton bands combined with a stretchable fabric to insure that the urine bag is secured firmly to the leg. A problem with this type of device is that it tightly and completely encompasses the leg and is therefore potentially uncomfortable if worn during warm weather. Additionally, any device that is supported by elastic utilizes a compressive force for support and is likely to be uncomfortable if worn for an extended period of time.

SUMMARY OF THE INVENTION

This invention provides a supporter for a urine collecting bag comprising a waistband and a partial pantleg that is attached to the waistband. The partial pantleg encircles the patient's thigh and is constructed of twilled fabric in the preferred embodiment. The partial pantleg has four buttons attached thereto for receiving a fluid collection bag typically constructed of vinyl or latex. The buttons are received in buttonholes which are typically integrally formed in the fluid collection bag. The buttons are placed on the partial pant leg in a manner that provides a buttonhole-to-button relationship that allows the fluid collection bag to expand as it fills with fluids. In the preferred embodiment, the pantleg is split vertically so that it can be laid open for receiving a patient's thigh. The portions of the partial pantleg adjacent to the split are adjustably attached together with a hook and loop fastener. The partial pantleg can be adjusted to accommodate thighs of different sizes. A tight fit is not necessary to maintain the drainage bag in position. Therefore, the partial pantleg may be worn for long periods of time without discomfort. An additional benefit of the partial pantleg is that it provides a soft breathable layer of fabric and prevents the typically vinyl or latex bag from making contact with the skin of the patient. The resulting drainage bag holder is a garment for supporting a fluid collection bag that can be worn comfortably by a patient for an extended period of time.

The use of buttons for attaching the drainage bag is beneficial because the drainage bag remains easily accessible. The use of buttons eliminates the difficulty of having to place a drainage bag within a pouch. The pouch type holder is an arrangement typically seen in existing drainage bag holders.

It is therefore and object of this invention to provide a urinary drainage bag holding system that enables a urinary drainage bag to be attached and removed with ease.

A further object of the invention is to provide a urinary drainage bag holding system that is comfortable for the patient and can be worn for extended periods of time. The present invention does not constrict the thigh of the patient and may be worn loosely and comfortably.

A yet further object of the invention is to provide a support for drainage bags used in all forms of ostomy, urological and incontinence situations.

BRIEF DESCRIPTION OF THE DRAWINGS

FIG. 2 is the leg underpant for supporting a fluid collection bag with a fluid collection bag attached thereto.

DETAILED DESCRIPTION OF THE PREFERRED EMBODIMENTS

According to the present invention, there is provided a leg underpant for supporting a fluid collection bag which supports, immobilizes and contains the fluid collection bag. The fluid collection bag is supported irrespective of the position of the wearer, the volume of fluid contained in the bag, the physical size of the wearer or whether the catheter emerges from the bladder through the urethra (a natural opening) or a cystotomy opening. The present invention allows the wearer freedom of movement to enable him to participate in any type of activity without fear of an accidental urine leakage due to a sudden disconnection resulting from shifting of the fluid collection bag. The present invention is designed so that it can be worn, adjusted or removed easily. Additionally, the present invention need not be tightly secured to the wearer's leg. It will therefore not constrict the wearer and may be worn comfortably for a long period of time.

Figure 1:
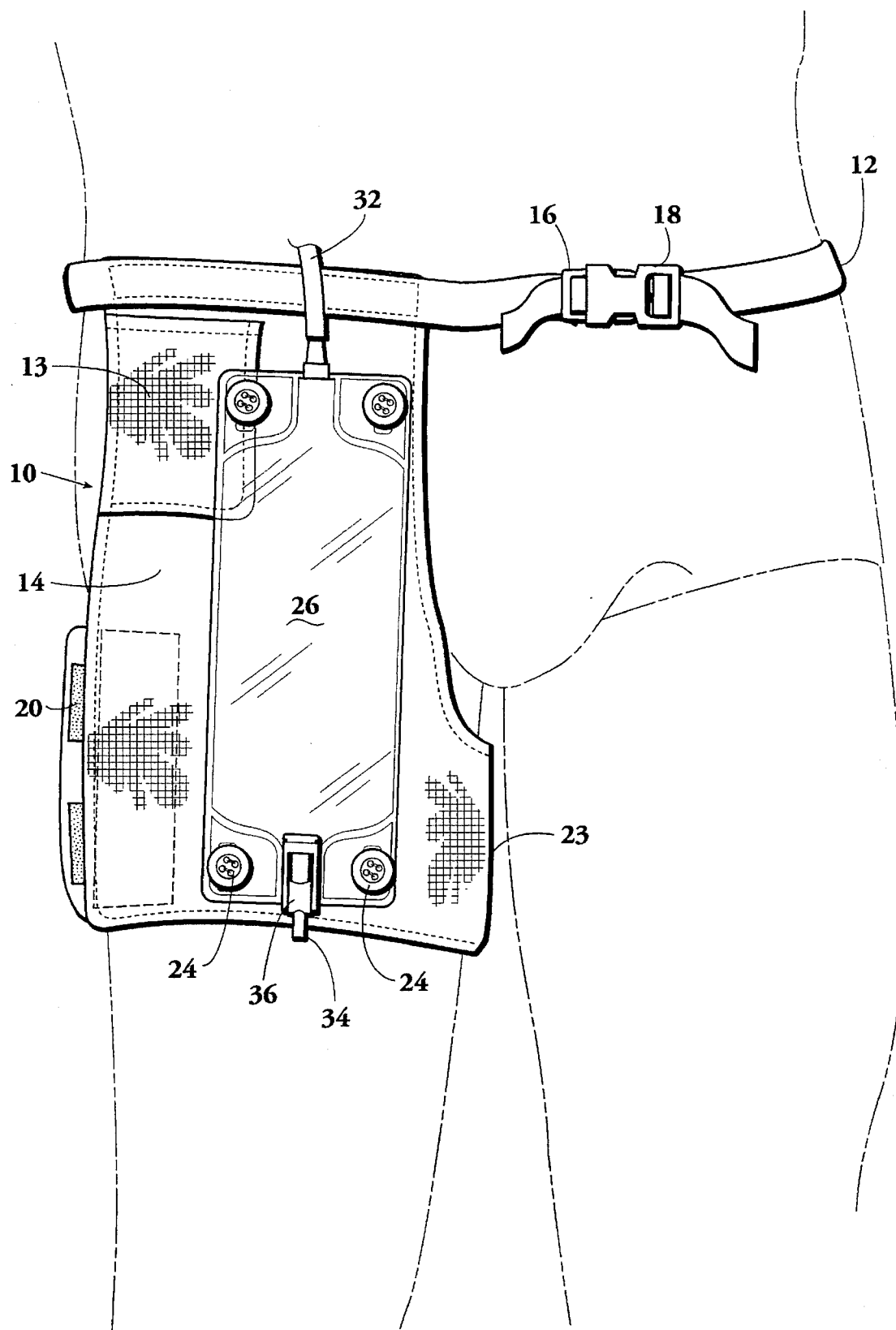
FIG. 1 shows the present leg underpant for supporting a fluid collection bag as worn by a patient.
Figure 4:
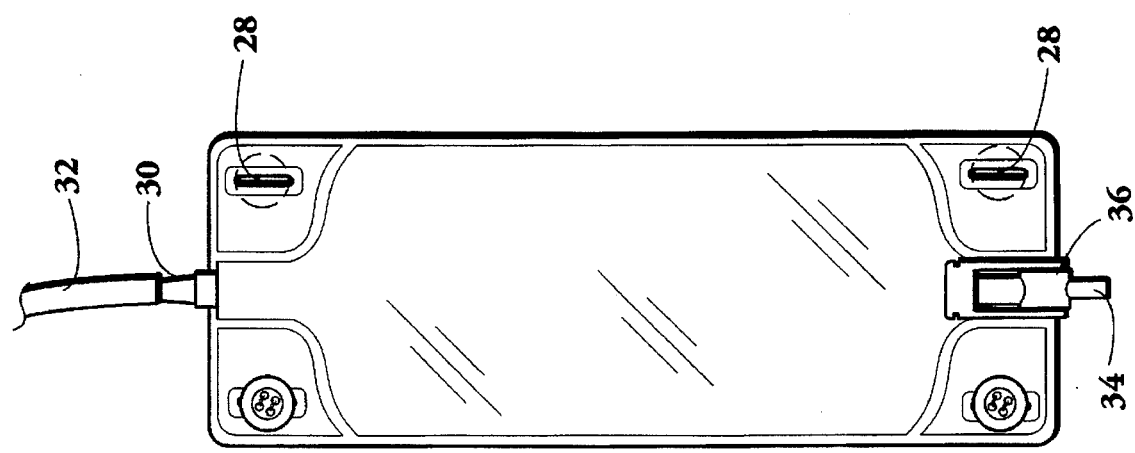
FIG. 4 shows a typical urine collection bag.
Figure 3:
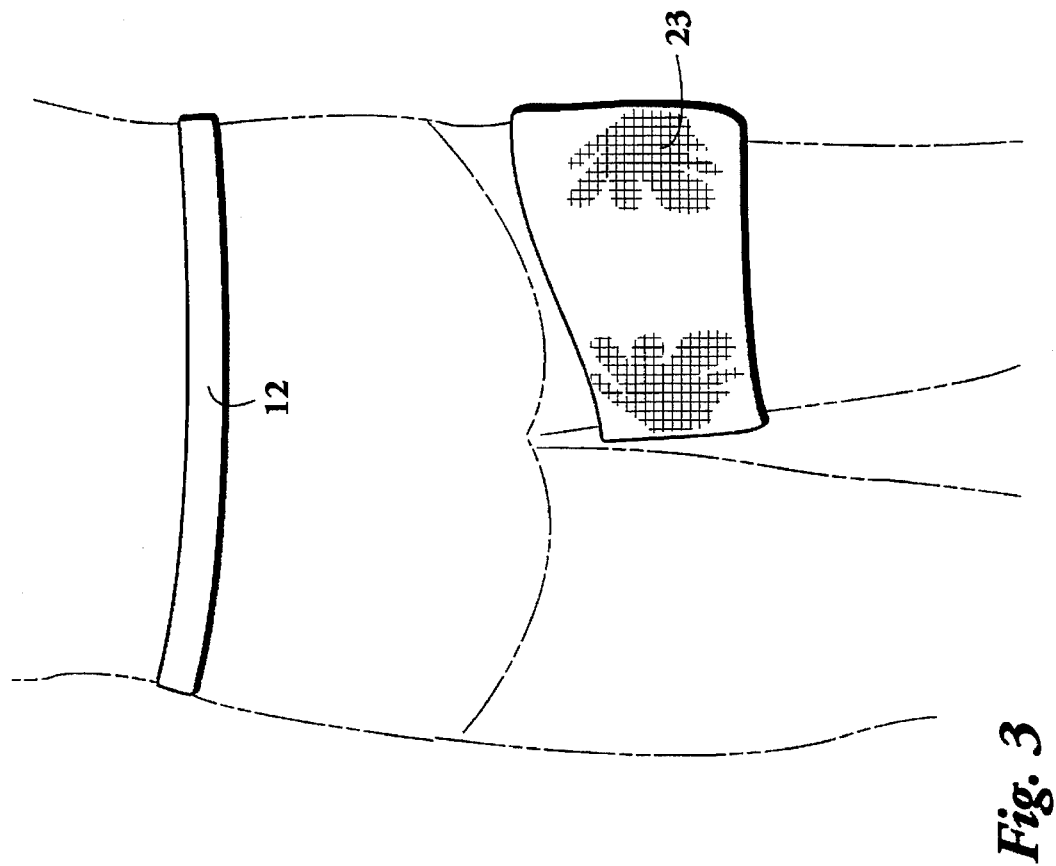
FIG. 3 shows a rear-view of a patient wearing a leg underpant for supporting a fluid collection bag.

Referring first to FIG. 1, shown is the holder for a urinary drainage bag designated generally 10 as worn by a person. As shown in further detail in FIG. 2, the holder comprises a waistband 12 for encircling the waist of the wearer. In the preferred embodiment, the waistband 12 is sewn onto the upper portion of partial pantleg 14 and is provided with adjustable fastening clips 16 and 18. A pocket 13 may be formed as a part of the upper portion for holding supplies, such as bandages, medication, dressing, tubing clamps, etc. as needed in conjunction with the use of the collection bag. The partial pantleg 14 is affixed to waistband 12 and is suspended therefrom. Hook and loop fasteners 20 and 22 are provided on lower portion 23 of partial pantleg 14 so that partial pantleg 14 can be adjusted for comfort and to accommodate thighs of different sizes. In the preferred embodiment, waistband 12 and partial pantleg 14 are comprised of twilled fabric. A plurality of buttons 24 are affixed to partial pantleg 14 for attaching urinary drainage bag 26 to partial pantleg 14. Urinary drainage bag 26 is shown isolated in FIG. 4. Typical urinary drainage bag 26 possesses buttonholes 28 formed integrally therewith. An inlet orifice 30 is provided on the upper portion of urinary drainage bag 26 for receiving elastomeric tubing Elastomeric tubing 32 communicates with the patient via a catheter and transports fluids to urinary drainage bag 26. Exit orifice 34 is provided on a lower area of urinary drainage bag 26 for emptying the urinary drainage bag. A swing valve shown as 36 is typically provided to allow the patient to open or close exit orifice 34. Care should be taken in affixing buttons 24 to partial pantleg so that buttons 24 are spaced to allow urinary drainage bag 26 to expand as it fills with fluid and not impart a force on buttons In summary, the leg underpant for supporting a fluid collection bag may be worn loosely around the patient's leg and is therefore more comfortable than existing devices that tightly affix a urine collection bag to a wearer's thigh. The weight of urine drainage bag 26 is supported by waistband 12. Partial pantleg and waistband 12 are constructed of soft twilled fabric in the preferred embodiment. This fabric provides a barrier between the patient's skin and the vinyl or plastic urinary drainage bag 26. As urinary drainage bag 26 expands as it becomes full, it does not impinge against buttons 24. Instead, buttonholes 28 slide past buttons 24 and no tugging or pulling on partial pantleg 14 takes place. The flexibility of the fabric accommodates the expanding walls of urinary drainage bag 26.

Whereas, the present invention has been described in relation to the drawings attached hereto, it should be understood that other and further modifications, apart from those shown or suggested herein, may be made within the spirit and scope of this invention.

What is claimed is:

1. A holder for a urinary drainage bag for securing the bag to a wearer's leg, and waist, comprising:

a waist band;

said holder affixed to said waist band and comprised of a non-elastic twilled fabric forming a lower partial single short pant leg surrounding and substantially covering said wearer's thigh of said leg; said pant leg being split forming a wide band that encircles said thigh and has two ends with an adjustable hook and loop fastener to connect the two ends about the thigh; and a means for attaching said urinary drainage bag to said pant leg.

2. A holder according to claim 1, wherein said means for attaching said urinary drainage bag to said holder is a plurality of buttons affixed to said partial pant leg.

* * * * *